United States Patent [19]

Noble et al.

[11] Patent Number: 5,130,027
[45] Date of Patent: Jul. 14, 1992

[54] STATIONARY MAGNETICALLY STABILIZED FLUIDIZED BED FOR PROTEIN SEPARATION AND PURIFICATION

[75] Inventors: Richard D. Noble, Boulder; Carl A. Koval, Lafayette; Lori Nixon; Geoffrey F. Slaff, both of Boulder, all of Colo.

[73] Assignee: The University of Colorado Foundation, Inc., Boulder, Colo.

[21] Appl. No.: 675,553

[22] Filed: Mar. 26, 1991

Related U.S. Application Data

[62] Division of Ser. No. 409,616, Sep. 19, 1989, Pat. No. 5,084,169.

[51] Int. Cl.$^5$ .................. B01D 15/08; B01D 35/06
[52] U.S. Cl. ................... 210/656; 210/635; 210/660; 210/695; 530/416; 530/417
[58] Field of Search .............. 210/198.2, 222, 507.1, 210/263, 506, 695, 905, 635, 656, 660, 695; 502/401, 402, 403, 404; 55/67, 100, 386, 2, 3, 4; 530/417, 416

[56] References Cited

U.S. PATENT DOCUMENTS

| | | | |
|---|---|---|---|
| 3,659,119 | 4/1972 | Tubeville | 210/222 |
| 4,115,927 | 9/1978 | Rosensweig | 55/100 |
| 4,675,113 | 6/1987 | Graves et al. | 210/695 |
| 4,780,113 | 10/1988 | Koslow | 210/695 |
| 4,861,705 | 8/1989 | Margel | 210/635 |
| 5,028,696 | 7/1991 | Torres et al. | 210/635 |
| 5,055,194 | 10/1991 | Goetz et al. | 210/222 |
| 5,084,169 | 1/1992 | Noble et al. | 210/222 |
| 5,084,184 | 1/1992 | Burns | 210/695 |

OTHER PUBLICATIONS

K. Mosbach et al., *Magnetic Ferrfluids for Preparation of Magnetic Polymers and Their Application in Affinity Chromatography*, 270 Nature, pp. 259-261 (1977).
R. Ronsenweig, *Fluidization: Hydrodynamic Stabilization with a Magnetic Field*, 204 Science, pp. 57-60 (1979).
R. Rosenweig, *Magnetic Stabilization of the State of Uniform Stabilization*, 18 I & EC Fundamentals, pp. 260-269 (1979).
R. Rosenweig et al, *Structure of Mangetically Stabilized Fluidized Solids*, in Continuum Models of Discrete Systems 4, OBrulin R. K. T. Hsieh eds. pp. 137-144 (1981).
M. Burns et al., *Continuous Affinity Chromatography a Magnetically Stabilized Fluidized Bed*, 1 Biotechnol. Prog, pp. 95-103 (1985).
M. Burns et al., *Application to Magnetically Stabilized Fluidized Beds to Bioseparations*, 6 Reactive Polymers, pp. 45-50 (1987).
J. Siegell, *Liquid-Fluidized Magnetically Stabilized Beds*, 52 Power Technology, pp. 139-148 (1987).
C. Lockmuller et al., *Affinity Separations in Magnetically Stablized Fluidized Beds: Synthesis and Performance of Packing Materials*, 22 Separation Science and Tech., pp. 2111-2125 (1987).
M. Burns et al., *Structural Studies of a Liquid-Fluidized Magnetically Stabilized Bed*, 67 Chem. Eng. Comm., pp. 315-330 (1988).
W. Resnick et al., *Magnetic Structural Effects on Flow Through Beds of Magnetizable Particles*, 24 IEEE Trans. on Magnetics, pp. 257-260 (1988).

*Primary Examiner*—Robert A. Dawson
*Assistant Examiner*—Sun Uk Kim
*Attorney, Agent, or Firm*—Beaton & Swanson

[57] ABSTRACT

Magnetically stabilized fluidized bed technology is utilized in conjunction with ion-exchange adsorption/-desorption processes in a method and system for isolating proteins from cell lysate. The invention also includes a magnetizable, porous, ion-exchange particle, and a method for producing the same, for use with the stationary magnetically stabilized fluidized bed protein isolation process.

5 Claims, 2 Drawing Sheets

STATIONARY MAGNETICALLY STABILIZED FLUIDIZED BED FOR PROTEIN SEPARATION AND PURIFICATION

This is a divisional of copending application(s) Ser. No. 07/409,616 filed on Sept. 19, 1989, now U.S. Pat. Ser. No. 5,084,169.

FIELD OF THE INVENTION

This invention relates to a method and system for performing chromatographic or adsorption/desorption isolations of proteins utilizing magnetically stabilized fluidized beds. Ion-exchange particles that have been made magnetizable are held in a stationary bed subjected to a radially uniform magnetic field as a solution containing proteins is passed upwardly through such bed. Following adsorption of the proteins onto the ion-exchange sites of the particles, an ionic or different pH solution is utilized to free the proteins from the particles.

BACKGROUND OF THE INVENTION

A fluidized bed is created when a gas or liquid is passed upwardly through a bed of solid particles with sufficient velocity wherein the drag forces of the gas or liquid counterbalance the gravitational forces on the particle and cause the bed to expand. A fluidized bed consists of particles that are completely submerged and levitated in the fluidizing fluid. In contrast, in a "packed" bed, the particles are fixed in space and have no translational freedom, due to their permanent contact with particles (or walls) surrounding them.

Ronald E. Rosensweig was the first to investigate the possibility of forming a "stabilized" fluidized bed by utilizing magnetizable particles and placing the system in a magnetic field. See R. Rosensweig, *Fluidization: Hydrodynamic Stabilization With a Magnetic Field*, 204 Science, pp. 57-60 (1979). Rosensweig's research concentrated on gas/solid systems. In gas/solid fluidized beds—used in heterogeneous chemical reactions such as hydrocarbon cracking—bubble formation greatly reduces the effectiveness of the process. Rosensweig discovered that by utilizing magnetizable particles in a radially uniform magnetic field, it was possible to create a "stabilized" fluid bed. Rosensweig, and others, have reported that the stabilization effect is more easily accomplished when the magnetic field runs parallel to the path of fluid flow.

A discussion of magnetically stabilized fluidized beds ("MSFB") in liquid/solid systems is found in J. H. Siegell, *Liquid-Fluidized Magnetically Stabilized Beds*, 52 Powder Technology, pp. 139-48 (1987). The effects of the magnetic stabilization are not as dramatic as those seen in the gas/solid systems, but nonetheless are quite significant. Siegell characterized four regimes in upwardly flowing solid particle beds: packed, stable, random motion and boiling.

In the absence of a radially-uniform magnetic field, a system utilizing the upward flow of fluid through a particle bed goes through three regimes as the velocity of fluid flow is increased. The "packed" regime is the same as in the presence of the magnetic field. At the point of "incipient fluidization"—where the velocity of the fluid creates drag forces that exactly counterbalance the gravitational effects on the particles—the random motion regime begins. With increased fluid flow velocity, the boiling regime can be seen.

The point of incipient fluidization is also the transition between the packed and stable regimes in MSFB. This point is not affected by the strength of the magnetic field applied. One can reach the stable regime either by first applying the magnetic field and then increasing the flow above the point of incipient fluidization, or by applying a magnetic field to the bed in the random motion regime already above the point of incipient fluidization.

When in the stable regime, the pressure drop in the bed remains constant with increased flow rate, the void volume of the bed increases, yet there is restricted motion of the particles due to the existence of the magnetic field. In the stable regime the bed of particles is clearly fluidized (expanded and flowable), yet it lacks the random motion traditionally associated with fluidized beds.

The effect of the magnetic field can be viewed roughly as creating a magnetic dipole in each particle, which causes it to become "sticky" in a direction parallel to the magnetic field lines. This produces what amounts to the formation of chains of beads parallel to the axis of the bed. For a detailed mathematical/theoretical investigation of the mechanism for MSFB, see Rosensweig et al., *Continuum Modes of Discrete Systems*4, O. Brulin and R. K. T. Hsieh, eds., North Holland Publishers, Amsterdam, 137-143 (1981).

References that describe the use of MSFB in conjunction with either adsorption/desorption or chromatographic separations are limited. Of course, the use of magnetizable particles in biochemical systems is relatively common. The references that disclose the use of MSFB have been restricted to affinity interactions.

Work described by Burns and Graves is directed towards a system using counter-current liquid/solid phase continuous affinity chromatography. See M. Burns and D. Graves, *Continuous Affinity Chromatography Using a Magnetically Stabilized Fluidized Bed*, 1 Biotechnol. Prog., pp. 95-103 (1985), M. Burns and D. Graves, *Application of Magnetically Stabilized Fluidized Beds to Bioseparations*, 6 Reactive Polymers, pp. 45-50 (1987); and M. Burns and D. Graves, *Structural Studies of a Liquid-Fluidized Magnetically Stabilized Bed*, 67 Chem. Eng. Comm., pp. 315-330 (1988). Rather than utilizing a stationary column of magnetizable particles, Burns and Graves anticipate using a system where the particles flow downwardly as the solution flows upwardly.

A paper by Lochmuller and Wigman also deals with the use of MSFB and affinity interactions. C. H. Lochmuller and L. S. Wigman, *Affinity Separations in Magnetically Stabilized Fluidized Beds*, 22 Separation Science and Technology, pp. 2111-2125 (1987). Although utilizing a magnetizable affinity particle, the particle used is of the non-porous, pellicular type. In such a system, only surface adsorption is possible.

Although affinity interactions can yield superb selectivity, it is an expensive technique for separating proteins. The great selectivity seen means that only single-protein specific particles can be prepared.

As mentioned above, the use of magnetizable particles is not unknown in biotechnology. The separation of proteins from mixtures by adsorption unto magnetizable particles—either hydrophobic, affinity or ion-exchange types—is often performed in batch preparations. The particle beads can be held in the bottom of a container with a magnet while excess solutions and wastes can be decanted out of the container. At the same time, the adsorbed proteins will remain with the particles. However, as is generally the case, for scale-up purposes it is usually more efficient to perform separations of this type on a column in a more or less continuous process.

An example of a procedure used to prepare a Sepharose based magnetizable particle using a ferrofluid is described in M. Mosbach and L. Andersson, *Magnetic Ferrofluids for Preparation of Magnetic Polymers and Their Application in Affinity Chromatography*, 270 Nature, pp. 259-261 (1977).

Combining the batch type adsorption processes into a column would provide certain advantages. However, by taking advantage of the MSFB, protein isolation performance can be greatly enhanced. Unlike many other separation schemes, fluidized beds are quite conducive to scaling up. No examples of a magnetizable, porous and stationary particle bed for ion-exchange adsorption/desorption or chromatography in an MSFB has been disclosed in the literature.

SUMMARY OF THE INVENTION

This invention relates to a method and apparatus for performing liquid/solid separations utilizing magnetically stabilized fluidized beds ("MSFB"). More particularly, this invention describes an improved method and system for separating proteins from a lysed cell mixture utilizing magnetizable, porous, ion-exchange particles. Utilizing MSFB allows the use of increased flow rates, the easy manipulation of the "fluid" particle bed, and the elimination of bed fouling due to cell solids.

A magnetizable particle is prepared according to the invention by placing agarose based ion-exchange particles in a ferrofluid solution for a significant period of time. The particles isolated after this treatment are suitable for use in this invention but have lost much of their ion-exchange capacity. Rather, these particles are discarded and the original ferrofluid solution is contacted for a shorter period of time with a fresh batch of agarose based ion-exchange particles.

The particles obtained from this second treatment have adsorbed a significant amount of the magnetite suspended in the ferrofluid yet have retained their ion-exchange capabilities. These particles are placed in a column that permits the flow of solution upwardly through the particle bed. The column is equipped with means for creating a magnetic field that runs parallel to the flow of solution through the column and is essentially radially uniform in the area of the particle bed.

Isolating proteins manufactured and held within cells generally involves a two step process after the cells have been lysed. The first step is a clarification of the lysate, where the cellular debris is removed from the mixture. The clarification is typically done by centrifugation of the lysate. The proteins in the clarified lysate are then isolated from the solution, often in a packed bed ion-exchange column or a batch-type interaction. Clarification always results in the reduction of protein yield.

In the present invention, the lysate may be introduced into the bottom of the MSFB column without clarification. The rate of flow and the strength of the magnetic field are adjusted so that a fluidized bed is generated. Due to the increased void area in the particle bed, the cell particulate matter will generally pass through the bed without fouling the particle bed or plugging flow. By increasing the magnetic field strength, the flow rate at which the stable and random motion regimes may be maintained is also increased. Increased flow rate can expedite the adsorption process without a parallel increase in pressure buildup.

Following the introduction of a "charge" of cell products, the protein in the mixture will be adsorbed into the porous ion-exchange particles. The amount of material to be included in the charge can be easily determined based on the flow rate and the quantity and binding capacity of the ion-exchange particles utilized. Once the cell matter has passed through the column, the ionic strength or pH of the solution flowing upwardly through the column is changed in order to alter the adsorption characteristics of the system and allow the proteins to desorb from the particle bed.

If an eluent gradient is utilized it is possible to obtain some protein specificity based on the ion-exchange characteristics of the individual proteins. The discharge from the top of the column may be collected and the solutions will be protein enriched.

When introducing the lysate into the column, it is not essential that the particle bed be in the stable regime. Depending on various factors, such as the binding capacity and rate of the particles and the solution flow rate, it may be desireable to maintain the bed in the random motion regime during the adsorption process. However, it is important to maintain the particle bed in the stable regime when desorbing the protein off the bed in order to assure that the protein is eluted from the column in a narrow band of solvent.

DETAILED DESCRIPTION OF THE PREFERRED EMBODIMENT

This invention describes an improved means for separating proteins from a lysed cell mixture utilizing porous, magnetizable, ion-exchange particles. The particles are maintained in a magnetically stabilized fluidized bed (MSFB) by the introduction of a radially uniform magnetic field with field lines parallel to the flow of solution. More generally, this invention describeds a method and system for separating certain chemical species from a mixture containing other chemicals and suspended particles by the use of adsorption/desorption or chromatographic processes combined with stationary MSFB's.

Figure 1:
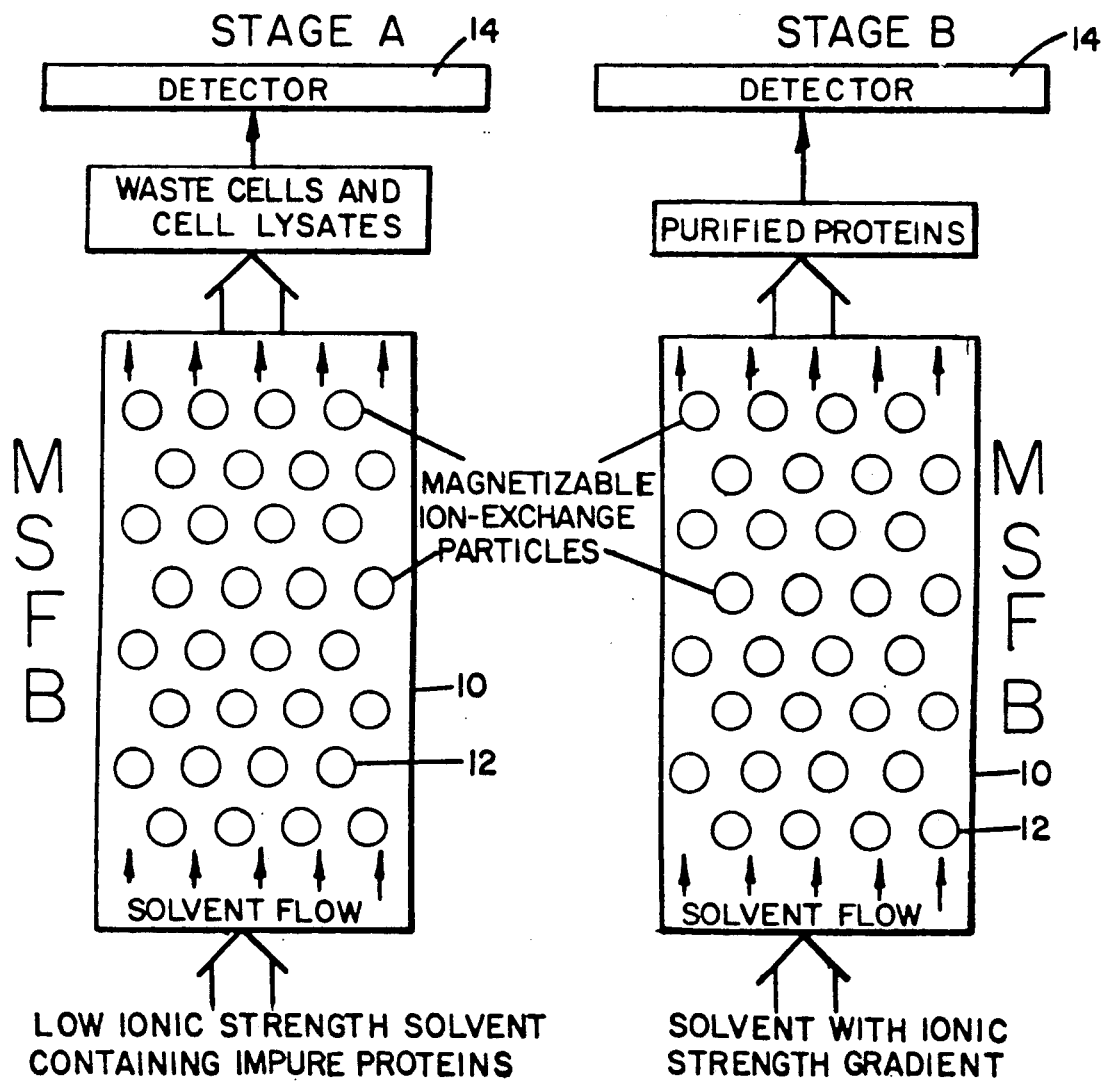
FIG. 1 shows a schematic representation of Stages A and B of an embodiment of the present invention.

A brief description of FIG. 1 will be used as an introduction to the various aspects of the present invention. FIG. 1 shows the two basic stages of the invention that utilize a MSFB. The support column 10 is a cylindrical tube held in a vertical position. In order to obtain a stable fluidized bed condition, it is imperative that the column be held in a vertical position and that the solution flow is also in a vertical direction.

The column 10 contains the magnetizable, ion-exchange particles 12. The particles 12 will be described in more detail below. The entire volume of the column's interior space is not filled by the particle bed. One of the characteristics of MSFB is that the void volume of the particle bed is increased. It is, therefore, necessary to have a significant amount of column volume when charging the particle bed.

In one embodiment, this invention relates to a method of isolating a specific protein or proteins from an impure feed solution. The feed solution will typically contain microscopic particles, such as whole and lysed cell components, as well other cell constituents.

Before introducing the protein feed solution onto the column, the stable or random motion MSFB regimes must be first obtained. These MSFB regimes can be obtained by either of two routes. The magnetic field may be applied and the solution flow increased above the point of incipient fluidization, or the velocity can be raised until a random motion or bubbling fluidized bed is achieved and then the magnetic field is applied. Determining what is the optimal magnetic field strength and solution flow rate velocity is discussed below. In some cases, the random motion regime may be preferred to the stable regime.

Once the designed MSFB regime has been attained, the protein feed solution will generally be applied to the column as seen in Stage A of FIG. 1. Due to the the column as seen in Stage A of FIG. 1. Due to the increased viscosity of the lysate, the flow rate of the solution must be decreased as the lysate is introduced onto the column. This decrease in velocity must be anticipated in order to assure that the particle bed be in the desired regime during the adsorption stage of the process. The feed solution is generally introduced in a pulse in a low ionic strength solvent. The proteins in the feed solution will adsorb to the ion-exchange sites of the particle beads. The cell waste and other products in the cell lysate will pass through the column in the solvent stream and may either be further treated or discarded. Because of the significantly increased void volume of the particle bed, the particulate matter in the cell will not tend to clog up the system.

The output of the column may be monitored by any number of types of detectors 14. A commonly used detector would be a UV-VIS spectrometric detector whereby the outlet stream is continuously monitored at a particular preset wavelength. During the first stage of the process, the detector can be set to monitor if there has been any protein "breakthrough," or simply to monitor when the cell wastes have been eluted from the column.

In Stage B of the process, the ionic strength or pH gradient of the solution, which does not include any lysate, flowing through the column is altered. This change should be accomplished while the column remains in a MSFB regime. Regardless of the regime the bed was in during Stage A of the process, the particle bed must be in the stable MSFB regime during Stage B. As the ionic strength of the solution increases or the pH changes, the ionic forces that bind the proteins to the ion-exchange sites of the particles are no longer as strong as the forces that drive the proteins into solution. By utilizing an ionic strength or pH gradient, individual proteins will desorb off the resin at different ionic strengths. By this means, some protein separation can also be obtained based on the ionic characteristics of the individual proteins. Again, the detector monitoring the column output may be used to determine what portions of solution exiting the column contain the isolated protein(s).

In some situations, it may be desirable to operate the column in a standard packed bed manner to perform the Stage B operation. If solution flow is introduced from the top of the column and exits the bottom, the elution of proteins will occur in the classic manner.

Figure 2:
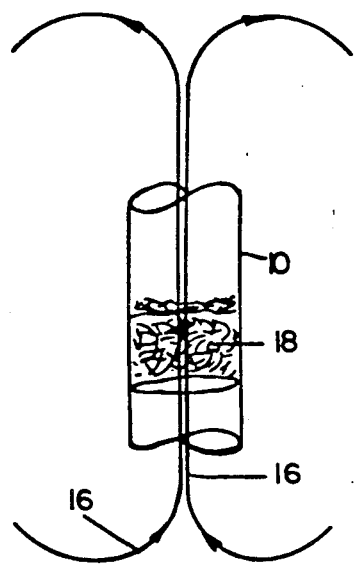
FIG. 2 is a schematic diagram of an embodiment of the present invention representing the relationship of the magnetic field to the particle containing columns.

FIG. 2 shows the orientation of the magnetic field 16 in the region of the particle bed 18 within the column 10. As can be seen, the magnetic field 16 runs axially in the region of the column, parallel to the flow of solution through the column. The appropriate magnetic field may be generated by utilizing horizontally held magnet coils that surround the column. In this manner, the magnetic field will be generally uniform across any radial cross-section of the particle bed 18. It is this type of magnetic field that allows for the optimal establishment of an MSFB. It would also be possible to use permanent magnets to generate the desired magnetic field.

Figure 3:
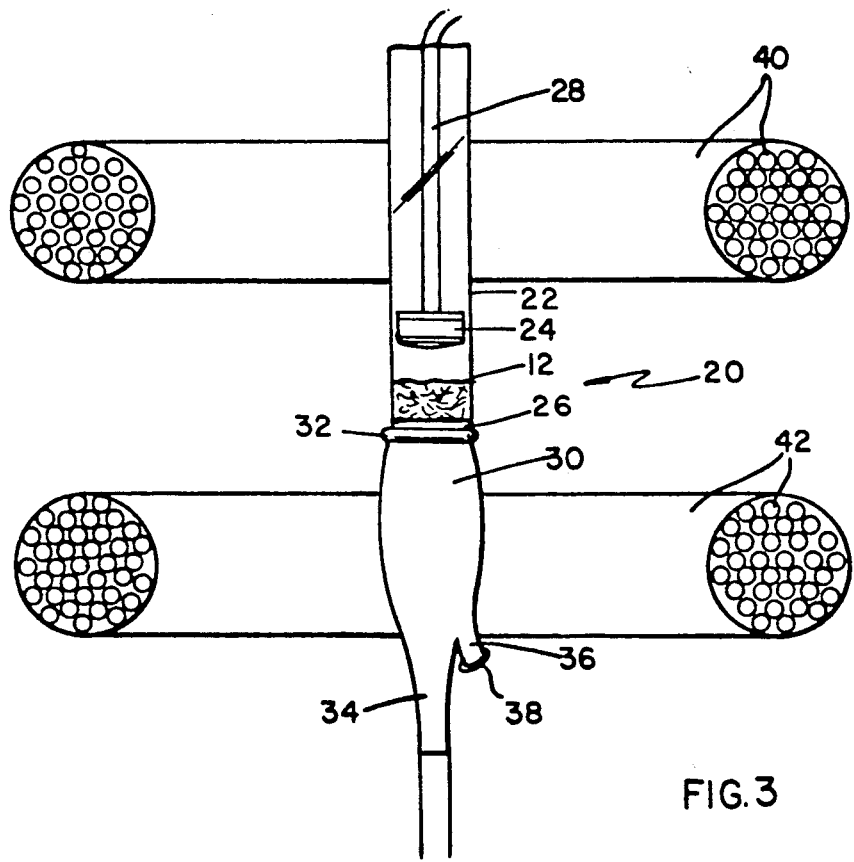
FIG. 3 is an elevational view of an apparatus used in an embodiment of the present invention.

FIG. 3 shows an embodiment of the apparatus used in the present invention. The apparatus 20, consists of a glass cylinder 22 that may be varied in capacity by the placement of stopper 24. The bottom of the cylinder 22 is defined by a frit 26 that supports the ion-exchange particles 12.

Exiting through the stopper 24, and in fluid communication with the interior of the cylinder is liquid outlet line 28. Note that a void exists between the top of the particle bed 12 and the bottom of the stopper 24.

Below the frit 26, the column chamber is in fluid communication with a glass funnel 30 that is held aginst the frit 26. An o-ring 32 between the funnel 30 and the frit 26 assures that an environmental seal is formed.

The glass funnel 30, has two inlet or solution introduction orifices. The first inlet 34 is in fluid communication with the source of solvent solution. A pump (not shown) may be employed to deliver solution to the first inlet 34. The second inlet 36 is shown covered by a rubber septum 38. The protein feed solution may be introduced into the solvent, and into the cylinder 22, from this inlet 34 via a syringe or other means.

The entire apparatus is surrounded by two magnet coils. One set of coils 40 is held horizontally at a position somewhat above the particle bed 12 and the second set of coils 42 is held horizontally at a position somewhat below such bed 12.

The embodiment of the apparatus of the invention utilized to generate the experimental results described below has the following dimensions. The diameter of the cylinder 22 is 1 inch, with a full height of 5 inches, the placement of the stopper 24 being adjustable within the cylinder 22, and the volume of the cylinder being about 75 ml. The exterior diameter of the magnet coils 40, 42 is about 6 inches and the coils are held about 3 inches from each other. The magnet coils 40, 42 each consist of 325 turns of 18 gauge copper wire. The frit 26 utilized is 0.25 inches thick with about 45 micrometer pores.

The preferred magnetizable, porous ion-exchange particles used in the present invention are prepared through a multistep process. One starting material is an agarose-based ion-exchange resin. The preferred material utilized is S-Sepharose Fast Flow manufactured by Pharmacia of Piscataway, N.J. The other solution used is a commerically available ferrofluid. A ferrofluid is an aqueous solution of small suspended magnetite particles ($Fe_3O_4$) that are coated with a cationic dispersing agent that prevents the magnetite particles from aggregating in solution. A ferrofluid may be purchased from Ferrofluids of Nashua, Mass.

The intimate mixture of the ion-exchange particles and the ferrofluid—following different procedures— may yield two distinct magnetizable products. An agitated solution of the ion-exchange particles in the ferrofluid for an extended period of time followed by decantion of the excess ferrofluid yields a first type of magnetizable particle (Type I). On visual inspection, these particles have a dark brown but transparent appearance (the untreated S-Sepharose Fast Flow is clear and transparent). The original ferrofluid should contain at least about 1.5% magnetite.

However, if the ferrofluid decanted from the mixture is subsequently mixed with a fresh batch of the ion-exchange particles, the resultant treated particles have a different appearance. This particle type (Type II) is brown and opaque, and is not smooth on its exterior surface. A high magnetic susceptibility, greater than $1 \times 10^{-4}$ cgs units, was seen for both types of particles. Magnetic susceptibility was measured as a packed bed, water filling the void volume of the bed.

Examination of the S-Sepharose starting material and the Type I and Type II magnetizable particles by scanning electron microscope shows a dramatic difference between the Type I and Type II particles. The untreated S-Sepharose and the Type I particles appear nearly identical at magnifications of about one thousand times. The particles have a smooth spherical surface. At the same magnification, the Type II particle has a drastically different appearance. The surface of the particles is rough and cratered, and the rough coating appears to completely cover the surface of the S-Sepharose particle.

The Type I particles have a decreased protein binding capacity relative to the untreated ion-exchange particles. The Type II particles, however, have an essentially identical protein adsorption capacity as the untreated S-Sepharose starting material. The preferred magnetized, porous, ion-exchange particles, having a high magnetic susceptibility and excellent protein binding characteristics, are the Type II particles.

Based on the results of the electron scanning microscope and protein binding experiments, it seems clear that in the Type I particles, the magnetite has entered the pore space of the particles and is blocking access to the ion-exchange sites therein. In the Type II particles, the magnetite is forming a surface covering, but the surface layer is not preventing the access of proteins into the pores of the particles.

A MSFB prepared utilizing the Type II magnetized, porous, ion-exchange resin may be used to isolate proteins from a solution by adsorption/desorption as described above in conjunction with FIG. 1. Of course, the present invention need not be so restricted as to the type a separation that can be performed or the particles utilized. For example, the isolation of certain organic chemical species from a reaction mixture could be susceptible to the use of MSFB utilizing magnetizable, porous stationary phases.

Possible explanations for the formation of the two different types of treated particles are only speculative. One mechanism, not intended to limit the scope of this invention, is that during the initial step, the smaller magnetite particles enter the pores of the S-Sepharose particles and associate with the ion-exchange sites within the material. In the second treatment, the remaining larger magnetite particles adhere onto the surface of the particles, yet aggregate in such a manner that access to the interior of the particles is not blocked.

As shown in the following examples, the Type II particles of this invention contain at least 5% by weight of magnetite, and have a magnetic susceptibility in excess of $1 \times 10^{-4}$ cgs units. In addition, the particles have a binding capacity that has been decreased from that of the untreated particle by less than 10%.

It is envisioned that the process utilized to create the Type II ion-exchange particles would lead to the same desireable characteristics if applied to any other generally available stationary phases used in chromatography or adsorption/desorption processes. These desireable properties and the method for obtaining such particles is not limited to ion-exchange materials as described herein.

A key element of the present invention is the use of porous rather than pellicular adsorption particles. Porous particles have a greatly increased capacity for adsorbing molecules. The Type II particles identified and described above have excellent magnetizability characteristics, yet also are porous and have a significant number of interparticle adsorption sites.

An interesting, yet currently unexplained, phenomena, is the fluidized bed properties of the Type II particles in the absence of a magnetic field. It is significantly easier to maintain the treated particles in a random motion fluidized bed regime than the untreated S-Sepharose particles.

The example given below relate specific experiments that have been performed relating to the production and characteristics of the magnetizable, porous, ion-exchange particles and the performance of the particles in MSFB adsorption/desorption isolation of a protein containing solution.

EXAMPLE 1

Preparation of Type I Resin 6.8 ml of moist S-Sepharose Fast Flow (90-165 micrometer particles) was added to 7 ml of ferrofluid (#EMG 607, about 1.7% by volume magnetite). This mixture was stirred for 19 hours. The particles isolated from this mixture are dark brown and translucent. These particles were found to have a magnetic susceptibility of $3 \times 10^{-4}$ cgs units. Based on the dry weight of the particles, the material contained 15.1% magnetite ($Fe_3O_4$).

EXAMPLE 2

Preparation of Type II Resin

The ferrofluid solution from the mixture of Example 1 is mixed with a fresh batch of 4.5 ml of the moist S-Sepharose particles and stirred for 4 hours. The particles isolated from this mixture are dark brown and opaque, and the surface appears "roughened" or as if coated with a fine brown powder. These particles were found to have a magnetic susceptibility of $4.5 \times 10^{-4}$ cgs units. Based on the dry weight of the particles, the material contained 9.3% magnetite.

EXAMPLE 3

Protein Binding Capacity

The protein binding capacities of the particles prepared in Example 1 and Example 2, as well as a sample of untreated S-Sepharose, were determined by exposing 1 ml of the various moistened particles to a Cytochrome-C containing solution. 20 ml of the solution contained 1 mg of the protein to each ml of solution, and the solution was held at pH 7. The change in concentration was monitored by visible absorption spectrometry. The results shown below indicate the milligrams of Cytochrome-C adsorbed by the particles after 5 minutes, a total of 20 mg available.

| Particle | mg. bound |
|---|---|
| Untreated S-Sepharose | 19.7 |
| Type I treated | 0.9 |
| Type II treated | 19.4 |

EXAMPLE 4

Establishment of MSFB Utilizing Type II Particles

The apparatus shown in FIG. 3, and described above, was used to create a magnetically stabilized fluidized bed. A study was made whereby the magnetic field and the solution flow rate were varied. For a given magnetic field strength, the flow rate was increased until the transition between the stable and random motion regimes was detected. The results of these experiment are shown below:

| Transition Velocity Linear Flow (cm/min) | Magnetic Field (gauss) |
|---|---|
| .58 | 41 |
| .73 | 56 |
| .83 | 70 |
| .96 | 88 |
| 1.08 | 105 |

EXAMPLE 5

Adsorption/Desorption of Cytochrome-C

An experiment wherein the Type II resin as prepared in Example 2 is held in a MSFB regime and a single protein (Cytochrome-C) is first adsorbed and then desorbed from the particles was performed. The apparatus shown in FIG. 3 and described above was utilized.

The solvent utilized in Stage A of the process consisted of an aqueous 0.025M phosphate buffer, pH 7. The desorption solvent in Stage B was a pH 7, 0.5M NaCl solution. The flow rate employed was 0.28 cm/min, the magnetic field was 77 gauss, and the bed height of the particle was 0.9 cm. The results of three runs is shown below:

|  | Run 1 | Run 2 | Run 3 |
|---|---|---|---|
| protein feed (mg) | 6.56 | 9.34 | 7.12 |
| protein loaded (mg) | 6.11 | 6.26 | 4.88 |
| protein recovered (mg) | 5.28 | 5.28 | 4.55 |

As indicated in the preceding Examples, an improved means for isolating proteins from a mixture utilizing stationary MSFB and a magnetizable, porous, ion-exchange particle bed is described. Of course, further applications of the invention beyond the Examples given are included with the scope of this invention. The claims below should not be limited by the embodiments described above.

We claim:

1. A method for isolating certain chemical species from a solution of chemicals and solids utilizing a stationary column comprised of magnetized, porous, particles capable of binding said chemical species and means for delivering said solution onto said column comprising:

subjecting said column to a radially-uniform magnetic field;

flowing said solution upwardly through said particles wherein said chemicals will bind to said particles, the flow rate and the strength of the magnetic field selected so that the flow rate is held within the stable or random motion fluidization regimes of said particles; and flowing a second solution through said particles wherein said chemicals will exit said column with said second solution.

2. The method of claim 1 wherein said chemical species are proteins in a lysed cell solution.

3. The method of claim 1 wherein said chemical species bind to said particles by being adsorbed into said particles.

4. The method of claim 1 wherein said chemical species bind onto the surface of said particles.

5. The method of claim 1, said particles including magnetite adhering predominantly to the outer surface of said particles without significantly affecting the adsorption capabilities of said particles.

* * * * *